United States Patent
Schouten et al.

(10) Patent No.: US 10,787,748 B2
(45) Date of Patent: *Sep. 29, 2020

(54) PROCESS FOR THE PREPARATION OF AN AROMATIC DICARBOXYLIC ACID

(71) Applicants: Avantium Knowledge Centre B.V., Amsterdam (NL); Synvina C.V., Amsterdam (NL)

(72) Inventors: Klaas Jan Pieter Schouten, Amsterdam (NL); Jan Cornelis Van Der Waal, Amsterdam (NL); Maria Varini, Amsterdam (NL); Gerardus Johannes Maria Gruter, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/575,783

(22) PCT Filed: May 20, 2016

(86) PCT No.: PCT/NL2016/050362
§ 371 (c)(1),
(2) Date: Nov. 20, 2017

(87) PCT Pub. No.: WO2016/186504
PCT Pub. Date: Nov. 24, 2016

(65) Prior Publication Data
US 2018/0142362 A1 May 24, 2018

(30) Foreign Application Priority Data

May 21, 2015 (NL) ..................... 2014841

(51) Int. Cl.
| | | |
|---|---|---|
| C25B 3/02 | (2006.01) | |
| C07D 307/68 | (2006.01) | |
| C07C 51/43 | (2006.01) | |
| C25B 11/04 | (2006.01) | |
| C25B 11/12 | (2006.01) | |

(52) U.S. Cl.
CPC ............ *C25B 3/02* (2013.01); *C07C 51/43* (2013.01); *C07D 307/68* (2013.01); *C25B 11/0415* (2013.01); *C25B 11/12* (2013.01)

(58) Field of Classification Search
CPC .................................................. C25B 3/02
USPC ................................................ 205/440, 442
See application file for complete search history.

(56) References Cited

U.S. PATENT DOCUMENTS

| | | |
|---|---|---|
| 3,819,503 A | 6/1974 | Casson et al. |
| 3,862,218 A | 1/1975 | Stautzenberger |
| 3,996,271 A | 12/1976 | Yokota et al. |
| 5,698,734 A | 12/1997 | Turner et al. |
| 8,242,292 B2 * | 8/2012 | Yutaka ............... C07D 307/68 549/485 |
| 8,658,810 B2 | 2/2014 | Partin et al. |
| 8,748,479 B2 | 6/2014 | Shaikh et al. |
| 8,791,278 B2 | 7/2014 | Shaikh |
| 2011/0092720 A1 * | 4/2011 | Yutaka ............... C07D 307/68 549/485 |
| 2013/0172611 A1 | 7/2013 | Bhattacharyya |
| 2013/0345452 A1 | 12/2013 | Janka et al. |
| 2016/0201204 A1 * | 7/2016 | Choi .................... C25B 3/02 205/427 |

FOREIGN PATENT DOCUMENTS

| | | | |
|---|---|---|---|
| PL | 161831 B2 * | 8/1993 | ............... C25B 3/00 |
| WO | 2011043660 A2 | 4/2011 | |
| WO | 2011043661 A1 | 4/2011 | |
| WO | 2015030590 A1 | 3/2015 | |
| WO | 2016112091 A1 | 7/2016 | |

OTHER PUBLICATIONS

Grabowski et al., "The Electrochemical Oxidation of 5-Hydroxymethylfurfural with the Nickel Oxide/Hydroxide Electrode," Electrochimica Acta (1995), vol. 36, No. 13, p. 1995. (Year: 1995).*
Van Effen et al., "A Study of Aldehyde Oxidation at Glassy Carbon, Mercury, Copper, Silver, Gold and Nickel Electrodes," J. Electroanal. Chem. (1979), vol. 103, pp. 383-397. (Year: 1979).*
Grabowski et al., "The Electrochemical Oxidation of 5-Hydroxymethylfurfural with the Nickel Oxide/Hydroxide Electrode," Electrochimica Acta (1991), vol. 36, No. 13, p. 1995. (Year: 1991).*
Grabowski, Grzegorz, et al; "The Electrochemical Oxidation of 5-Hydroxymethylfurfural with the Nickel Oxide/Hydroxide Electrode;" Electrochimica Acta, vol. 36, No. 13, p. 1995; Printed in Great Britain in revised form on Jan. 31, 1991.
P. Parpot, et al; "Electrochemical Investigations of the Oxidation-Reduction of Furfural in Aqueous Medium Application to Electrosynthesis;" Electrochimica Acta, vol. 49 (2004), pp. 397-403; www.sciencedirect.com; May 6, 2003.

(Continued)

*Primary Examiner* — Edna Wong
(74) *Attorney, Agent, or Firm* — Suiter Swantz pc llo

(57) ABSTRACT

An aromatic dicarboxylic acid of chemical formula HOOC—Ar¹—COOH is prepared in a process wherein a feedstock comprising at least an aromatic aldehyde compound of chemical formula (1): OHC—Ar¹—COOH, wherein Ar¹ represents an arylene or heteroarylene moiety, and an aqueous electrolyte are provided; the feedstock and the aqueous electrolyte are introduced into an electrolytic cell comprising electrodes, wherein at least one of the electrodes comprises a non-noble metal and/or an oxide and/or a hydroxide thereof and/or carbon; and the aromatic aldehyde compound of formula (1) is oxidized electrochemically to yield the aromatic dicarboxylic acid.

17 Claims, No Drawings

(56) References Cited

OTHER PUBLICATIONS

PCT Search Report and Written Opinion; PCT/NL16/50362 filed on May 20, 2016, Published as WO 2016/186504 dated Nov. 24, 2016; 11 pages.

R.A.F. Tomas et al., p-Xylene Oxidation to Terephthalic Acid: A Literature Review Oriented toward Process Optimization and Development, Chemical Reviews, Jun. 14, 2013, pp. 7421-7469, vol. 113, No. 10, ACS Publications, American Chemical Society.

Vuyyuru et al., Oxidation of biomass derived 5-hydroxymethylfurtural using heterogeneous and electrochemical catalysis, Catalysis Today, Jun. 8, 2012, pp. 144-154, vol. 195, Elsevier B.V.

Chadderdon et al., Electrocatalytic oxidation of 5-hydroxymethylfurfural to 2,5-furandicarboxylic acid on supports Au and Pd bimetallic nanoparticles, Green Chemistry, Apr. 24, 2014, pp. 3778-3786, vol. 16, The Royal Society of Chemistry.

H.G. Cha et al., Combined biomass valorization and hydrogen production in a photoelectrochemical cell, Nature Chemistry, Mar. 9, 2015, pp. 1-6, Macmillan Publishers Limited.

\* cited by examiner

PROCESS FOR THE PREPARATION OF AN AROMATIC DICARBOXYLIC ACID

The present invention relates to a process for the preparation of an aromatic dicarboxylic acid. More in particular it relates to a process for the preparation of furandicarboxylic acid and terephthalic acid by means of electrochemical oxidation.

The electrochemical oxidation of aromatic compounds to aromatic acids has been subject of several research activities. A study into the feasibility of the electrochemical oxidation of 5-hydroxymethylfurfural (HMF) using a Pt electrode has been reported in K. Vuyyuru et al., Catal. Today, 195 (2012) 144-154. It was found that a fraction of HMF could be converted into diformylfuran and a small quantity (≤1%) of 2,5-furandicarboxylic acid (FDCA). In D. J. Chadderdon et al., Green Chem., 2014, 16, 3778-3786, the use of an electrode of gold and palladium nanoparticles supported on carbon black was found to enhance the yield of FDCA from HMF in electrochemical oxidations. By employing various ratios of gold and palladium and various potential differences a conversion of HMF to FDCA could be obtained in an FDCA yield of up to 83%. It appeared that use of a gold electrode was favorable for the conversion to FDCA whereas the use of a palladium electrode led to FDCA at high potentials only. From HMF various intermediate compounds were produced, including 5-hydroxymethyl-2-furancarboxylic acid and 5-formyl-2-furancarboxylic acid (FFCA). The complete conversion into FDCA was found not to be possible. Hence it is still required to subject the electrochemically oxidized product to complicated purification.

H. G. Cha et al., report in Nature Chemistry, in the article titled: "Combined biomass valorization and hydrogen production in a photoelectrochemical cell", (published online 9 Mar. 2015) the complete electrochemical conversion of HMF into FDCA using 2,2,6,6-tetramethylpiperidine 1-oxyl (TEMPO) as a mediator and catalyst. The electrodes used were a gold anode or a photoanode of $BiVO_4$ and platinum counter electrodes. In this study it was found that the electrochemical oxidation of FFCA into FDCA was the slowest of the reaction steps and thus the rate-limiting step for the TEMPO-mediated oxidation of HMF into FDCA. It is evident that the use of the expensive noble metal electrodes and the additional use of a mediator such as TEMPO constitute disadvantages of this process.

In the earlier2 patent PL 161831 the electrochemical oxidation of HMF into FDCA was reported in a yield of 71%, using as anode a nickel plate coated with nickel oxide and as cathode a nickel plate. The potential was 0.6 V measured in relation to a calomel electrode. This finding is confirmed in G. Grabowski et al., Electrochimica Acta, 36 (1991) 1995. The use of a non-noble metal electrode, such as nickel, lead or copper, has also been investigated for the oxidation of furfural into furoic acid. It was found that the best conditions for preparative electrochemical oxidation included the use of a nickel anode, yielding up to 80% furoic acid (cf. P. Parpot et al., Electrochimica Acta, 49 (2004) 397-403).

The above described studies illustrate that there is a need for the complete conversion into FDCA that does not require the use of noble metal electrodes and/or the use of intermediates.

US 2013/0172611 discloses a process for the preparation of terephthalic acid from 4-carboxybenzaldehyde (4-CBA) by contacting a pure 4-CBA stream, an ionic liquid-comprising solvent, a bromine source, a cobalt-containing catalyst and an oxidizing agent to produce terephthalic acid. The terephthalic acid produced still contains some 4-CBA. Therefore several purification methods are mentioned in US2013/0172611, including additional oxidation steps. Alternatively, the terephthalic acid is subjected to filtration, washing, drying and hydrogenation steps, or to a solvent contacting step, from which the terephthalic acid may be obtained by precipitation and/or crystallization.

Surprisingly it has now been found that feedstocks that comprise an aromatic aldehyde compound that comprise a carboxyl substituent can easily be oxidized in an electrolytic cell to complete conversion into an aromatic dicarboxylic acid.

Accordingly the present invention provides a process for the preparation of an aromatic dicarboxylic acid of chemical formula $HOOC\text{—}Ar^1\text{—}COOH$, comprising;
    providing a feedstock comprising at least an aromatic aldehyde compound of chemical formula (1)

$$OHC\text{—}Ar^1\text{—}COOH \quad\quad (1),$$

wherein $Ar^1$ represents an arylene or heteroarylene moiety, and an aqueous electrolyte;
    introducing the feedstock and the aqueous electrolyte into an electrolytic cell comprising electrodes, wherein at least one of the electrodes comprises a non-noble metal and/or an oxide and/or a hydroxide thereof and/or carbon; and
    oxidizing the aromatic aldehyde compound of formula (1) electrochemically to yield the aromatic dicarboxylic acid.

Although the prior art documents mainly relate to the conversion of HMF into FDCA or furfural into furoic acid in limited yields, it has now been found that the conversion of the aldehyde function of an aromatic aldehyde into the carboxylic function over a non-noble metal or carbon electrode when the aromatic aldehyde is substituted with another carboxyl group, is easier than the oxidation of the mono-substituted aldehyde, i.e. furfural, or the furfural derivative containing a hydroxymethyl substituent, i.e. HMF, leading to substantially complete conversion. The aromatic aldehydes may contain a hydrocarbon aromatic ring or a heteroaromatic ring. Hence, the aromatic aldehyde compound of formula (1) may be derived from a mono- or polycyclic hydrocarbon aromatic compound, such as benzene, naphthalene, anthracene or phenanthrene, but also from oxygen-, nitrogen- or sulfur-containing heteroaromatic compounds, such as furan, benzofuran, dibenzofuran, pyridine, quinoline, isoquinoline, or thiophene. Preferably $Ar^1$ is selected from phenylene, furylene and pyridylene moieties.

By "non-noble metal" is understood any metal that does not belong to the group commonly regarded as noble metals, i.e. gold, silver and the platinum-group metals ruthenium, rhodium, palladium, osmium, iridium and platinum.

It was found that the process according to the present invention can be applied to a feedstock that comprises only the aromatic aldehyde compound. Then it is still possible to obtain virtually complete conversion of the aldehyde compound into the aromatic dicarboxylic acid. Such a reaction may take a considerable time which makes the commercial application of such a reaction expensive and thus unfeasible. It has been found that it is very convenient that the aqueous electrolyte also contains some aromatic dicarboxylic acid. Such an aromatic dicarboxylic acid suitably is represented by the chemical formula (2)

$$HOOC\text{—}Ar^2\text{—}COOH \quad\quad (2),$$

wherein $Ar^2$ is the same or different from $Ar^1$ and represents an arylene or heteroarylene moiety. $Ar^2$ is suitably selected independent of the meaning of $Ar^1$. $Ar^2$ can thus also comprise a mono- or polycyclic hydrocarbon aromatic compound, such as benzene, naphthalene, anthracene or phenanthrene, but also an oxygen-, nitrogen- or sulfur-containing heteroaromatic compound, such as furan, benzofuran, dibenzofuran, pyridine, quinoline, isoquinoline, or thiophene. Preferably, $Ar^2$ is selected from phenylene, furylene and pyridylene moieties. More preferably, $Ar^1$ and $Ar^2$ are the same. Even more preferred are compounds of chemical formulae (1) or (2) wherein $Ar^1$ and $Ar^2$ are the same and are selected from furylene and phenylene. $Ar^1$ and $Ar^2$ or either of them may contain further substituents. Preferably these other substituents do not react under influence of the potential in the electrolytic cell. Therefore, the use of alkyl, alkoxy, hydroxyalkyl, formyl and similar substituents are not preferred. Suitable other substituents may include nitro groups or halogen atoms. However, preferably, $Ar^1$ and $Ar^2$ only contain aldehyde and/or carboxylic acid groups. Further, the aldehyde group and the carboxylic acid groups may be positioned at various positions in the aromatic ring. Very advantageously, when the aromatic aldehyde compound comprises a furylene moiety, the aldehyde group and the carboxylic acid group are positioned at the 2 and 5 positions. When $Ar^1$ represents a phenylene group, the aldehyde and carboxylic acid groups are preferably present in the 1 and 4 positions. In these embodiments the attractive compounds 2,5-furandicarboxylic acid (FDCA) and terephthalic acid, respectively, can be produced. In these situations $Ar^2$ advantageously represents 2,5-furylene or 1,4-phenylene, respectively, so that the aromatic dicarboxylic acid that is present in the feedstock is the same as the aromatic dicarboxylic acid that is prepared from the aromatic aldehyde compound of formula (1). In this way the process according to the present invention is used as a purification step for the product that may be obtained by using a conventional oxidation of an aromatic starting material. Since the relative amount of the aromatic aldehyde compound is thus reduced the residence time of the feedstock in the electrolytic cell can also be limited. This enhances the economic feasibility of the use of the electrochemical oxidation. A significant advantage of the present invention resides in that a conventional oxidation tends to have a relatively low selectivity at high conversion. When the oxidation is brought to substantial completion, the selectivity of the eventual product may be relatively high, but the yield of this product is rather low since part of the starting material and product may have been converted to further oxidation products such as carbon monoxide and carbon dioxide. It is known that at increasing temperature and increased residence time the conversion of starting material ends up in a loss of product. This is e.g. known from R. A. F. Tomas et al., Chem. Rev., 113 (2013) pp 7421-7469, wherein it is stated that after oxidation to the diaromatic carboxylic acid decarboxylation may occur at further oxidation. Such decarboxylation does not only occur in the aromatic acids, but also in the solvent when this is a carboxylic acid, such as acetic acid. The present invention allows a relatively low conversion to the eventual product. Any intermediate product, which includes the aromatic aldehyde compound, will be further oxidized to the aromatic dicarboxylic acid via electrochemical oxidation, whereas the kiss of product due to the formation of carbon monoxide and carbon dioxide is avoided. This therefore results in an increased overall yield of the aromatic dicarboxylic acid.

The feedstock of the process of the present invention comprises an aromatic aldehyde compound and, optionally, an aromatic dicarboxylic acid. The feedstock may comprise other components. Suitable alternative components include other intermediate compounds in the oxidation of disubstituted aromatic or heteroaromatic compounds. Hence when $Ar^1$ is phenylene, alternative compounds may include xylene, e.g. p-xylene, substituted benzyl alcohol compounds or diformylbenzene. When $Ar^1$ is furylene, alternative components in the feedstock may include HMF, diformyl-furan or hydroxymethyl-furancarboxylic acid. Preferably, the feedstock comprises the aromatic aldehyde compound of formula (1) and the aromatic dicarboxylic acid of formula (2) in an amount of at least 90% wt, preferably, at least 95% wt, based on the weight of the feedstock. Other compounds that may be present in the feedstock are esters of aromatic aldehyde compound of chemical formula (1) and/or of the aromatic dicarboxylic acid of chemical formula (2). The ester compound may be the monoester or the diester of the aromatic dicarboxylic acid, preferably the monoester so that the polarity and thus solubility of the compound is significant. The alcohol component of the esters is suitably provided by a lower alkyl group, i.e. an alkyl group with 1 to 4 carbon atoms.

When the feedstock comprises an aromatic aldehyde compound and an aromatic dicarboxylic acid, the relative amounts of the aromatic aldehyde compound and the aromatic dicarboxylic acid in the feedstock may vary within wide ranges, e.g. from 1000:1 to 1:100, preferably from 100:1 to 1:10, based on a weight by weight ratio. The present process is especially suited for a post-oxidation reaction of an intermediate product when a compound, e.g. HMF, an ether or ester thereof, or p-xylene, is oxidized in a different way in a first oxidation step. It has been known for a long time to oxidize xylene to terephthalic acid with an oxygen-containing gas using a catalyst system comprising cobalt, manganese and bromine (cf. U.S. Pat. No. 3,996,271). Also the oxidation of HMF or the ethers or esters of HMF with a similar catalyst system is known and has been described in WO 2011043660 and WO 2011043661. These oxidation reactions tend to lead to incomplete conversions. In order to increase the yield of the desired aromatic dicarboxylic acid the reaction mixture may be subjected to oxidation in a number of oxidation zones. Such a sequence of oxidation zones has been described in U.S. Pat. No. 8,791,278. In the process according to U.S. Pat. No. 8,791,278 HMF or an ether or ester thereof is oxidized in the presence of a Co, Mn and Br-containing catalyst in a primary oxidation zone so that an FDCA-containing product is obtained. The product contains other intermediate products. Therefore, the FDCA-containing product is separated into a mother liquor and a slurry stream, and the slurry stream is subjected to further oxidation in a secondary oxidation zone. The secondary oxidation zone operates at a higher temperature than the primary oxidation zone. In an alternative embodiment the product of the primary oxidation zone is without further separation passed into the secondary oxidation zone. In both embodiments this sequence entails that the feedstock for the secondary oxidation zone is to be heated further. The application of the secondary oxidation zone runs the risk that the product may be further oxidized to carbon monoxide and carbon dioxide, thereby lowering the yield of desired product. Moreover, the experimental data in U.S. Pat. No. 8,791,278 show that the process described therein still yield noticeable amounts of FFCA. A drawback of the presence of FFCA or 4-carboxybenzaldehyde (4-CBA) resides in the fact that these impurities are extremely difficult to separate by crystallization from the desired product, i.e. 2,5-furan dicarboxylic acid or terephthalic acid, respectively. This is shown in e.g. U.S. Pat. No. 8,658,810 describing a purification process of crude FDCA by esterification and subsequent separation of the various esters, and U.S. Pat. No. 8,748,479 describing a process wherein crude FDCA is hydrogenated and the hydrogenation products are separated.

When the process according to the present invention is applied to the product of the catalytic oxidation of xylene, dimethylfuran, HMF or an ester or ether thereof, intermediate products such as 4-carboxybenzaldehyde (4-CBA) or FFCA can easily be further oxidized to terephthalic acid and FDCA. The process according to the present invention is thus advantageously used as a purification step for the product that is obtained in a conventional oxidation of aromatic starting materials such as xylene, dimethylfuran, HMF or an ester or ether thereof. The present process then provides a simple economic method to complete conversion of the intermediates that tend to be difficult to separate.

Therefore, it is advantageous when the process according to the present invention is applied to the reaction product of a conventional oxidation of an aromatic compound such as xylene, dimethylfuran, HMF, or an ester or ether of HMF. Whereas the application of a sequence of oxidation zones tends to be cumbersome in that further heating is required and still no complete conversion can be obtained easily, the present process allows for the electrochemical oxidation at mild conditions whereas complete oxidation of the aromatic aldehyde compound of formula (1) can be obtained. The feedstock for the process of the present invention, therefore, suitably has been obtained by the oxidation of $Ar^1$—$(R^1)_2$, wherein $Ar^1$ has the meaning above and each $R^1$ is independently selected from methyl, hydroxymethyl, alkoxymethyl, carbonyloxymethyl and formyl. When $R^1$ represents carbonyloxymethyl, the substituent is suitably an alkylcarbonyloxymethyl group, in which the alkyl group contains 1 to 4 carbon atoms. Suitable substituents are acetoxymethyl and propionoxymethyl. When $R^1$ represents alkoxymethyl, the alkyl group has suitably from 1 to 4 carbon atoms, and is preferably methyl or ethyl. The oxidation of $Ar^1$—$(R^1)_2$ has suitably been carried out by an oxygen-containing gas in the presence of a catalyst comprising cobalt, manganese and optionally bromine. The oxidation has suitably been conducted in a solvent comprising an aliphatic carboxylic acid or an aliphatic carboxylic anhydride, in particular acetic acid or acetic anhydride. The ratio of the aromatic aldehyde compound to aromatic dicarboxylic acid is suitably in the range of 5:1 to 1:500, on a weight by weight basis. Since the present process can suitably be applied as a purification step of the product of a conventional oxidation the ratio of the aromatic aldehyde compound to aromatic dicarboxylic acid is suitably in the range of 1:9 to 1:100, on a weight by weight basis. Since the electrochemical oxidation according to the present invention readily leads the conversion to completion, there is no necessity to maximize the yield in the conventional oxidation. When the oxidation product contains up to 10% wt of the aromatic aldehyde compound, such an amount can still easily be converted into the desired aromatic dicarboxylic acid.

After the oxidation of $Ar^1$—$(R^1)_2$ the resulting oxidized product is typically subjected to some form of purification before the thus purified product is used as feedstock for the process according to the present invention. During the purification, catalyst components, e.g. cobalt, manganese and/or bromine compounds, are removed from the oxidation product, e.g. by washing. It is known that during the oxidation of the compound $Ar^1$—$(R^1)_2$ also by-products are formed that cause coloration. In US 2013/0345452 it has been made the objective of the process described therein to reduce the amount of colorants, also known as color bodies, in the preparation of FDCA from HMF or an ether or ester thereof over a catalyst containing cobalt, manganese and bromine. In conventional processes these colorants have to be removed by one or more re-crystallizations. In the process according to US 2013/0345452 the colorants are removed by means of hydrogenation of crude FDCA. Surprisingly, it has now been found that during the oxidation of the feedstock of the present invention in the electrolytic cell also colorants are removed. The process according to the present invention therefore not only increases the yield of the desired aromatic dicarboxylic acid by converting the aromatic aldehyde compound into the desired aromatic dicarboxylic acid, but it also reduces the content of colorants, which facilitates the isolation of colorless product from the resulting product in the electrolytic cell. This constitutes a significant additional advantage of the present process.

The skilled person will know what components are required to form an electrolytic cell. The cell comprises an anode, a cathode and an electrolyte. The anode and cathode are connected to a power supply, capable of applying a potential over the anode and cathode. The electrolytic cell may further be provided with a reference electrode. The reference electrode may be a standard hydrogen electrode and provides an indication for the potential to cause the oxidation reaction. Typically the electrolytic cell is operated in the absence of a reference electrode.

The electrolytic cell may be a divided cell or an undivided cell. In a divided cell a separation has been established between the electrolyte that is in contact with the anode and the electrolyte that is in contact with the cathode. Such a separation may be achieved by a semi-porous membrane, made from e.g. sintered glass, porous porcelain, polytetrafluoro ethylene (PTFE or Teflon®) or polyolefin such as polyethylene or polypropylene. In an undivided cell the aqueous electrolyte and the feedstock are in contact with both the anode and the cathode. Such an undivided cell is easier to operate than a divided cell; thus that represents an advantage. Operation in an undivided cell enables not only the oxidation of the aromatic aldehyde compound of formula (1), but it also makes it possible that undesired reactions take place at the cathode, e.g. the reductive coupling of aldehydes to a diol. Since such reactions do not take place when a divided cell is being used, the application of a divided cell is especially preferred.

The electrodes need not be prepared from noble metals, such as gold, platinum or palladium, as prescribed in the processes according to the prior art. In accordance with the present invention at least one of the electrodes comprises a non-noble metal and/or carbon. The use of non-noble metals, their hydroxides and/or their oxides is preferred. In this specification the noble metals are selected from ruthenium, rhodium, palladium, silver, osmium, iridium, platinum, and gold. The non-noble metals are all those metals other than these noble metals. The non-noble metals suitably include the base metals, lead, iron, copper, tin, nickel and compounds or alloys thereof. A suitable alloy of iron is e.g. stainless steel, comprising i.a. a significant amount of chromium. The electrolytic cell may contain an anode and a cathode that both contain a non-noble metal. However, the material, a non-noble metal, does not need to be the same in both the anode and the cathode. It was found that such other non-noble metals could be beneficial as cathode material in reducing the formation of by-products when such cathodes were also in contact with the aromatic aldehyde. This can e.g. be the case when an undivided cell is being used.

Another very suitable material for application as electrode is carbon, in particular graphite. The cathode material is suitably carbon. The electrode comprising the non-noble metal does not need to contain the metal in its elemental form. The electrode may suitably comprise noble metal with the oxide and/or hydroxide thereof. Such an electrode may be similar to the one used in the above-mentioned article by Grabowski et al. (Electrochimica Acta, 36 (1991) 1995). It has been found that the use of nickel or copper as material for the electrodes is advantageous. Accordingly, the electrolytic cell has been provided with at least one electrode that comprises a non-noble metal, its oxide and/or its hydroxide, which non-noble metal is nickel or copper. When reference is made to a non-noble metal-containing electrode this indicates that the electrode in question may comprise the non-noble metal in elemental form, as its oxide and/or as its hydroxide. The non-noble metal-containing, e.g. nickel, electrode can be in the form of a rod. However, in order to enhance the surface of the electrode, the non-noble metal-containing, e.g. nickel, electrode is suitably in the form of a plate, a mesh, a metal foam or in the form of small particles on a carrier, such as a carbon carrier. The non-noble metal can be used as the material for either of the anode or the cathode, preferably for the anode. As indicated above, carbon is suitably used as material for the cathode. Carbon may also be used as substrate for an electrode onto which metal has been impregnated.

The electrolytic cell contains an aqueous electrolyte. In order to facilitate the solubility of the aromatic dicarboxylic acid in the electrolyte, the aqueous electrolyte suitably is an alkaline solution. The alkalinity facilitates the dissolution of the dicarboxylic acid, both as the product and also when a dicarboxylic acid is added in the feedstock, and also enhances the solubility of the aromatic aldehyde compound of formula (1) that also comprises a carboxyl group. Suitably, the alkaline solution comprises an alkaline compound selected from an alkali metal hydroxide, alkali metal carbonate, alkali metal bicarbonate, ammonia, ammonium carbonate, ammonium bicarbonate, a trialkylamine and combinations thereof. The use of weak acids and bases, such as carbonate and bicarbonate, has the advantage that they provide a buffering effect. The trialkylamine suitably contains alkyl groups with 1 to 4 carbon atoms, preferably 1 or 2 carbon atoms. Suitable amines include trimethyl amine and triethyl amine. The use of organic amines is advantageous since these compounds can be relatively easily recovered from the aqueous electrolyte after the electrochemical oxidation. Suitable recovery methods include extractive distillation.

The aqueous electrolyte may comprise such an amount of an alkaline compound that the aqueous electrolyte, in spite of the presence of the aromatic dicarboxylic acid that is produced and/or that is added in the feedstock having chemical formula (2) is still alkaline. The pH of the aqueous electrolyte is suitably in the range of 7.5 to 13. When the pH is sufficiently high, the formation of additional dicarboxylic acid by the oxidation of the aromatic aldehyde compound does not render the electrolyte neutral or acidic. To the electrolyte a buffer solution may have been added. Such an addition, however, is not required. When the aromatic dicarboxylic acid of formula (2) being a weak acid is added to the feedstock, the electrolyte is already buffered. Large amounts of alkaline compounds tend to have the effect that such large amounts needs to be removed after the electrochemical oxidation.

The aqueous electrolyte does not need to be alkaline. It is feasible to employ a mixture of the feedstock in water to which no base has been added. The electrolyte may then be formed by the combination of water and feedstock, and the ions are provided by the carboxyl function in the aromatic aldehyde compound and the aromatic dicarboxylic acid compound, if such an aromatic dicarboxylic acid is added to the feedstock. Thus, the pH of the aqueous electrolyte may be acidic, e.g. having a value of 0.5 to 7.0. A drawback of using water without the addition of a base resides in the reduced solubility of the feedstock as well as a lower conductivity of the electrolyte.

Therefore, the aqueous electrolyte suitably contains such an amount of alkaline compound that the solubility of the carboxylic acid and the conductivity of the electrolyte are satisfactory, whilst the amount of alkaline compound is lower than the equivalent amount of carboxyl groups in the carboxylic acid-containing composition. The pH of such solutions may then vary from e.g. 1.0 to 7.5. The amount of alkaline compound may thus be selected within wide ranges. Preferably, the amount is in the range of 0.1 to 3.0 equivalents per equivalent carboxyl group in the feedstock, more preferably from 0.5 to 1.5 equivalents per equivalent carboxyl group.

The electrolyte does not need to consist of water and ions only. The electrolyte may conveniently also comprise one or more organic diluents. Suitable diluents are water-miscible organic compounds, such as alcohols, aldehydes, ketones or sulfoxides. Suitable diluents include one or more of methanol, ethanol, n-propanol, i-propanol, n-butanol, i-butanol and t-butanol, formaldehyde, acetone and dimethylsulfoxide. The electrolyte suitably contains water at least in an amount of 5% wt, based on the weight of the electrolyte, more preferably at least 50% wt, and most preferably at least 90% wt, based on the weight of the electrolyte.

The process according to the present invention does not require the presence of a mediator such as TEMPO in order to bring the conversion to completion. It was found that the electrochemical oxidation of the aromatic aldehyde compound of formula (1) using at least one non-noble electrode already yields the desired result. However, if the skilled person would desire to add a mediator, it may be done. The disadvantage is not only the additional cost, but also the need to remove this chemical from the electrolyte after the electrochemical oxidation. Therefore, the aqueous electrolyte preferably does not contain 2,2,6,6-tetramethylpiperidine 1-oxyl. The aqueous electrolyte preferably does not contain any mediator compound.

The conditions in the electrolytic cell can be determined by the person skilled in the art. It is evident that the potential and current in the electrolytic cell must be of a sufficient magnitude to produce the chemical reactions desired. These reactions include the conversion of the aldehyde functionality in the aromatic aldehyde compound of formula (1) into a carboxyl functionality on the anode and the reduction of water molecules to molecular hydrogen on the cathode. The potential difference between anode and cathode in the electrolytic cell is suitably below 10V, more preferably below 1.23 V. By applying a voltage below 1.23 V the electrolysis of water is avoided. The desired voltage can be provided by installing a predetermined current or current density. The current may vary within wide limits as determined by the shape, size and other parameters of the electrolytic cell. Typically, the current density is varied between 0.1 mA/cm$^2$ and 10 A/cm$^2$, preferably from 0.2 mA/cm$^2$ to 1 A/cm$^2$. The total current is adapted according to the surface of the smallest electrode. The reaction is typically prolonged at these conditions until the desired reactions take place.

The oxidation of the aromatic aldehyde compound can be achieved at a wide range of reaction conditions. The temperature and pressure can be ambient. Obviously, the skilled person may apply elevated temperatures and pressures if he would so desire. For instance, if the feedstock becomes available at elevated temperature and pressure from a preceding oxidation of a compound $Ar^1—(R^1)_2$ these prevailing temperatures and pressures may be maintained in the electrolytic cell during the oxidation of the aromatic aldehyde compound. Accordingly, the aromatic aldehyde compound of formula (1) is suitably oxidized at a temperature in the range of 10 to 250° C. and at a pressure in the range of 0.5 to 20 bar. The use of elevated temperatures has the advantage that the solubilities of the aromatic aldehyde compound and of the aromatic dicarboxylic acid are increased. The residence time of the feedstock in the electrolytic cell is also selected such that a sufficient charge has been supplied to the anode to allow for a substantially complete conversion of the aldehyde functionality to the carboxyl functionality. Evidently, factors that influence residence time of the feedstock in the electrolytic cell include the concentration of the aromatic aldehyde compound in the electrolyte, the current and the potential, current density, the surface area of the electrodes, the degree of homogenization of the electrolytes and the volume of the electrolytic cell. Typically, the residence time of the feedstock in the electrolytic cell is in the range of 0.1 to 24 hrs.

The process according to the present invention can be carried out in a batch mode. In a batch mode the residence time may suitably be in the range of 0.25 to 24 hrs, preferably, from 0.5 to 8 hrs. Preferably, the process is conducted in a continuous mode. An example of a continuous electrolytic cell has been described in U.S. Pat. No. 3,819,503. Although the known continuous electrolytic cell has been described for the manufacture of oxyhalogen compounds, a similar cell can be used for the continuous oxidation of the aromatic aldehyde compound according to the present invention. In a continuous electrolytic cell the residence time may be shortened; suitably the residence time is then in the range of 0.1 to 10 hrs, preferably from 0.25 to 8 hrs.

After the oxidation of the aromatic aldehyde compound a reaction medium is obtained that comprises aromatic dicarboxylic acid and electrolyte. The electrolyte tends to be alkaline. Therefore, the aromatic dicarboxylic acid obtained after the electrochemical oxidation of the aromatic aldehyde compound of formula (1) is suitably recovered by acidizing the aqueous electrolyte and allowing the aromatic dicarboxylic acid to precipitate. As indicated above, most if not all of the colorants have been removed during the oxidation in the electrolytic cell. Therefore, the precipitated product is virtually colorless.

The invention will be further illustrated by means of the following examples.

EXAMPLE 1

In 50 milliliters of 0.5 M NaOH in water FFCA was dissolved in a concentration of 50 mmol/liter. A divided electrolytic cell consisting of two compartments separated from each other by means of a porous glass frit, was used. The FFCA solution was placed in one compartment, i.e. the anode compartment, of the divided electrolytic cell. The anode compartment was further provided with an anode, i.e. a nickel plate. The other compartment, i.e., the cathode compartment, was provided with an aqueous solution of 0.5M NaOH and a cathode consisting of a nickel mesh. Both compartments were stirred. At room temperature, i.e. about 20° C., a current was applied on the electrodes. The current was 6.4 mA, corresponding with a current density of 0.8 mA/cm$^2$. The voltage measured at the anode was 0.4-0.7 V versus reference Ag/AgCl electrode. The current was continued for 6.7 hours. At the anode the FFCA was oxidized to FDCA. At the cathode hydrogen evolved. After 6.7 hours the content of the solution in the anode compartment was analyzed. The conversion of FFCA was measured as molar percentage of aldehydes that have disappeared. Apart from FFCA and FDCA, only a trace of 5-hydroxymethyl-furan-2-carboxylic acid (HMFCA) was detected in the solution of the anode compartment. HMFCA is believed to be the product of the Cannizarro reaction that may have taken place in the anode compartment. Since only a trace of HMFCA was found, it is understood that any HMFCA that is formed is also further oxidized to FDCA at the anode. The aldehyde conversion is shown in Table 1 below.

A similar experiment was conducted with a solution comprising 50 mM/L FFCA and 50 mM/L FDCA in 50 milliliters 0.5 M NaOH solution. This solution was also subjected to electrochemical oxidation. After 6.7 hrs the solution in the anode compartment was analyzed. The compounds found were FFCA and FDCA. The results are shown in Table 1.

For comparison two experiments were conducted with 50 mM/L furfural in 0.5 M NaOH solution and 50 mM/L furfural and 50 mM/L furoic acid in 50 mL of 0.5 M NaOH. The reaction with furfural was continued for 5.0 hours; the reaction with furfural and furoic acid lasted 6.7 hours. The conversion of the aldehyde is shown in Table 1.

TABLE 1

| Experiment No. | Reagent | Aldehyde conversion, % |
|---|---|---|
| 1 | FFCA | 89.3 |
| 2 | FFCA + FDCA | 90.0 |
| 3 | Furfural | 62.1 |
| 4 | Furfural + furoic acid | 71.9 |

The experiments show that the electrochemical oxidation of an aromatic aldehyde that contains a carboxyl substituent proceeds faster and leads to a more complete conversion than the corresponding unsubstituted aromatic aldehyde.

EXAMPLE 2

To show the influence of the total charge, reaction temperature, and the composition of the feedstock, a series of experiments were carried out in substantially the same way as described for the experiments in Example 1. The electrolyte was 0.5 M NaOH solution. The feedstock and the concentration thereof (in mmoles per liter NaOH solution) have been shown in Table 2. Table 2 also shows the reaction temperature as well as time of the feedstock in the electrolytic cell when the maximum conversion was obtained. The electrodes both consisted of nickel mesh. The current applied amounted to 22.4 mA, corresponding with a current density of 0.8 mA/cm$^2$ and a potential at the anode of 0.4-0.8 V versus a reference Ag/AgCl electrode. In experiment No. 9 a feedstock was used that consisted of crude FDCA, obtained in the oxidation of methoxymethylfurfural with oxygen in acetic acid using a Co, Mn and Br-containing catalyst. The crude FDCA contained about 1% wt FFCA, based on the total crude FDCA, and minor amounts of color bodies. The Table also shows the conversion of the aromatic aldehyde compound.

TABLE 2

| Exp. No. | Feedstock | Reaction temperature, ° C. | Residence time, hr | Aldehyde conversion, % |
|---|---|---|---|---|
| 5 | 50 mM FFCA | 20 | 5.6 | 99.8 |
| 6 | 50 mM FFCA + 50 mM FDCA | 20 | 5.6 | 99.8 |
| 7 | 50 mM FFCA + 50 mM FDCA | 75 | 3.7 | 99.2 |
| 8 | 5 mM FFCA + 45 mM FDCA | 20 | 1.7 | 100.0 |
| 9 | 50 mM crude FDCA | 20 | 1.0 | 100.0 |

Comparison between Experiment Nos. 1 and 2 of Table 1 with Experiment Nos. 5 and 6 of Table 2 shows that when the charge passed through the cell is increased, the conversion is further enhanced to virtual completion. Comparison between Experiment Nos. 6 and 7 shows that an increased reaction temperature increases the reaction rate. Experiments 8 and 9 show the suitability of the present process in the purification of mixtures of FDCA and FFCA. Since the oxidation of FFCA also converts any HMFCA that may be formed due to a Cannizarro reaction, the yield of FDCA is optimized. Whereas the feedstock of experiment No. 9 shows a brown/yellow color, the product after electrochemical oxidation is almost colorless, indicating that major color bodies have been removed.

EXAMPLE 3

The use of an undivided electrolytic cell was also shown in Experiment Nos. 10-13. A glass vessel used as an undivided electrolytic cell was filled with 50 mL of a solution of feedstock as indicated in Table 4 having a concentration of the number of millimoles indicated per liter aqueous 0.5 M NaOH, an anode and a cathode. The material of the anode was a nickel mesh as indicated in Example 2, and the cathode was made of nickel mesh or carbon paper. A current of 22.4 mA was applied between the anode and cathode. The electrochemical oxidation was conducted at room temperature, i.e. 20° C., for a period as shown as the residence time in Table 3. The feedstock, cathode material and aldehyde conversion in the aqueous electrolyte after the residence time indicated are also shown in Table 3. The electrolyte was also varied by using 0.5 M NaOH in water or 0.5 M triethyl amine (TEA) in water. The feedstock in experiment Nos. 11-13 was crude FDCA, including 1% wt FFCA, based on the total crude FDCA and minor amounts of color bodies.

TABLE 3

| Exp. No. | Feedstock | Cathode material | Electrolyte | Residence time, hr | Aldehyde conversion, % |
|---|---|---|---|---|---|
| 10 | 50 mM FFCA + 50 mM FDCA | Ni mesh | NaOH | 5.6 | 97.9 |
| 11 | 150 mM crude FDCA | Ni mesh | NaOH | 5.6 | 98.4 |
| 12 | 50 mM crude FDCA | Carbon paper | NaOH | 3.5 | 100.0 |
| 13 | 50 mM crude FDCA | Carbon paper | TEA | 5.1 | 99.1 |

In addition to a virtually complete conversion of the aldehyde compound, the resulting product in experiment Nos. 10-13 also showed considerably less coloring, indicating that also color bodies were oxidized.

EXAMPLE 4

To show that the present process can also be applied to aromatic aldehyde compounds other than FFCA, two further experiments were conducted on a feedstock comprising benzaldehyde and benzoic acid in one experiment and on 4-carboxybenzaldehyde (4-CBA) and terephthalic acid in the second experiment. The experiments were conducted in a way similar to the experiments in Example 2. The divided electrolytic cell was used. Both the anode and the cathode were nickel mesh electrodes. The electrolyte was 0.5M NaOH. The reaction temperature was 20° C. and the current was 22.4 mA. The electrochemical oxidation was continued for 5.6 hours.

The concentration of the materials (number of millimoles per liter) and the results are shown in Table 5.

TABLE 5

| Experiment No. | Feedstock | Aldehyde conversion, % |
|---|---|---|
| 14 | 5 mM benzaldehyde + 45 mM benzoic acid | 71.4 |
| 15 | 50 mM 4-CBA + 50 mM terephthalic acid | 81.6 |

The results show that also when benzaldehyde is further substituted with a carboxyl group the electrochemical oxidation with a non-noble metal-containing electrode is facilitated.

EXAMPLE 5

To show the suitability of non-noble metals other than nickel, four experiments were performed in substantially the same way as described for the experiments in Example 1. The electrolyte was 0.5 M NaOH solution. The feedstock was a solution of crude FDCA (containing 1% wt FFCA) with a concentration of 50 mM per liter 0.5 M aqueous NaOH. The anode was either a stainless steel plate (Exp. No. 16), a tin plate (Exp. No. 17), a copper mesh (Exp. No. 18) or carbon paper (Exp. No. 19). The cathode was a nickel mesh, as used in Exp. No. 2. The reaction temperature was 20° C. The current applied amounted to 22.4 mA.

For comparison reasons the same electrochemical conditions were applied to a platinum mesh anode and a nickel mesh cathode (cf. Exp. No. 20). The total conversion after 5.6 hours was recorded for Exp. Nos. 16, 19 and 20, whereas the total conversion of aldehyde for Exp. No. 17 was reached after 3.2 hours and for Exp. No. 18 already after 0.4 hours. The results are summarized in Table 5

TABLE 5

| Exp. No. | Anode material | Residence time, hr | Aldehyde conversion, % |
|---|---|---|---|
| 16 | Stainless steel | 5.6 | 92.3 |
| 17 | Tin plate | 3.2 | 100 |
| 18 | Copper mesh | 0.4 | 100 |
| 19 | Carbon paper | 5.6 | 78.0 |
| 20 | Platinum mesh | 5.6 | 33.0 |

The results show that non-noble metals that are used as anode material perform better than noble metals, even when the noble metal is present as anode with a larger surface area. The copper electrode is particularly effective. Also the carbon electrode is significantly more efficient than the platinum electrode.

The invention claimed is:

1. A method for the preparation of an aromatic dicarboxylic acid of chemical formula HOOC-$Ar^1$-COOH, comprising:
   providing an aqueous electrolyte and a feedstock wherein the feedstock comprises at least an aromatic aldehyde compound of chemical formula (1)

OHC-$Ar^1$-COON  (1), wherein $Ar^1$ represents an arylene or heteroarylene moiety, and wherein the aqueous electrolyte contains an aromatic dicarboxylic acid represented by the chemical formula (2)

HOOC-$Ar^2$-COOH  (2), wherein $Ar^2$ is the same or different from $Ar^1$ and represents an arylene or heteroarylene moiety;
   introducing the feedstock and the aqueous electrolyte into an electrolytic cell comprising electrodes, wherein at least one of the electrodes comprises a non-noble metal and/or an oxide and/or a hydroxide thereof and/or carbon; and
   oxidizing the aromatic aldehyde compound of formula (1) electrochemically to yield the aromatic dicarboxylic acid.

2. The method according to claim 1, wherein $Ar^1$ and $Ar^2$ are the same or different and are independently selected from phenylene, furylene and pyridylene moieties.

3. The method according to claim 1, wherein $Ar^1$ and $Ar^2$ are the same.

4. The method according to claim 1, wherein the feedstock has been obtained by oxidation of $Ar^1$-$(R^1)_2$, wherein $Ar^1$ has the meaning as defined in claim 1 and each $R^1$ is independently selected from methyl, hydroxymethyl, alkoxymethyl, carbonyloxymethyl and formyl.

5. The method according to claim 4, wherein the oxidation of the $Ar^1$-$(R^1)_2$ has been carried out by an oxygen-containing gas in presence of a catalyst comprising cobalt, manganese and optionally bromine.

6. The method according to claim 5, wherein the oxidation of the $Ar^1$-$(R^1)_2$ has been conducted in a solvent comprising an aliphatic carboxylic acid or an aliphatic carboxylic anhydride.

7. The method according to claim 1, wherein the electrolytic cell is a divided cell.

8. The method according to claim 1, wherein the non-noble metal is nickel or copper.

9. The method according to claim 1, wherein the carbon is used as a cathode material in the at least one of the electrodes of the electrolytic cell.

10. The method according to claim 1, wherein the aqueous electrolyte further contains an alkaline solution.

11. The method according to claim 10, wherein the alkaline solution comprises an alkaline compound selected from an alkali metal hydroxide, alkali metal carbonate, alkali metal bicarbonate, ammonia, ammonium carbonate, ammonium bicarbonate, a trialkylamine and combinations thereof.

12. The method according to claim 1, wherein the aqueous electrolyte does not contain 2,2,6,6-tetramethylpiperidine 1-oxyl.

13. The method according to claim 1, wherein the potential difference between the electrodes in the electrolytic cell is at most 10 V.

14. The method according to claim 1, wherein the aromatic aldehyde compound of formula (1) is oxidized at a temperature in the range of 10 to 250 ° C. and at a pressure in the range of 0.5 to 20 bar.

15. The method according to claim 1, wherein the residence time of the feedstock in the electrolytic cell is in the range of 0.1 to 24 hours.

16. The method according to claim 1, wherein the method is conducted in a continuous mode.

17. The method according to claim 1, wherein the aromatic dicarboxylic acid obtained after the electrochemical oxidation of the aromatic aldehyde compound of formula (1) is recovered by acidizing the aqueous electrolyte and allowing the aromatic dicarboxylic acid to precipitate.

* * * * *